United States Patent [19]

Southwick

[11] Patent Number: 5,137,036

[45] Date of Patent: Aug. 11, 1992

[54] SMOKING COMPOSITIONS CONTAINING A VANILLIN-RELEASE ADDITIVE

[75] Inventor: Everett W. Southwick, Richmond, Va.

[73] Assignees: Philip Morris Incorporated, New York, N.Y.; Philip Morris Products Inc., Richmond, Va.

[21] Appl. No.: 565,126

[22] Filed: Aug. 10, 1990

[51] Int. Cl.$^5$ .......................... A24B 3/12; C07C 69/95
[52] U.S. Cl. ...................................... 131/277; 560/53
[58] Field of Search .................... 560/53; 131/277, 276

Primary Examiner—V. Millin
Attorney, Agent, or Firm—James E. Schardt; George A. Depaoli

[57] ABSTRACT

This invention provides smoking compositions which contain a novel di-vanillyl ester flavorant-release additive.

Under cigarette smoking conditions, a combustible filler and/or paper wrapper additive such as di-ethylvanillyl oxalate pyrolyzes and releases ethylvanillin as a volatile flavorant component of the cigarette smoke.

26 Claims, No Drawings

SMOKING COMPOSITIONS CONTAINING A VANILLIN-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228, 3,943,943; 3,586,387; 3,379,754; and the like.

J. C. Leffingwell et al "Tobacco Flavoring For Smoking Products" (R. J. Reynolds Publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke and in cases consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. Nos. 3,332,428 and 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,117,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe α-hydroxyesters which as additives in smoking compositions pyrolyze into volatile aldehyde and ester flavorants under smoking conditions.

Of specific interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethylvanillyl-D-glucoside yields ethylvanillin and levoglucosan as pyrolysis products.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel di-vanillyl and di-ethylvanillyl esters which are adapted to be incorporated into cigarette filler and/or paper wrapper components, and which under normal smoking conditions release vanillin or ethylvanillin as a volatile flavorant compound of the cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

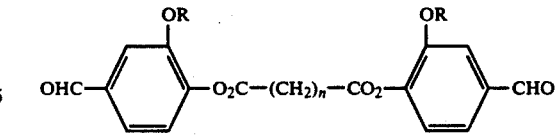

where n is an integer in the range of 0–4, and R is methyl or ethyl.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

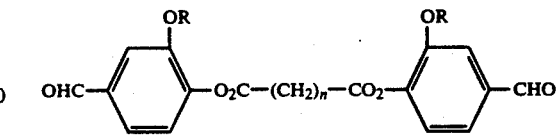

where n is an integer in the range of 0–4, and R is methyl or ethyl.

A cigarette smoking product in accordance with the present invention typically contains between about 0.01–5 weight percent of flavorant-release additive in the paper wrapper. The additive can be present as a surface coating or absorbed component of the paper wrapper, and/or the additive can be incorporated as a component of the adhesive formulation which is utilized to seal the sideseam of cigarette paper wrappers.

In a further embodiment an invention cigarette product contains between about 0.01–5 weight percent of flavorant-release additive in the paper wrapper, and contains between about 0.0001–5 weight percent of flavorant-release additive in the combustible filler, based on the weight of filler.

A present invention flavorant-release additive which is incorporated in smoking compositions as described above is a low volatility compound which under normal smoking conditions pyrolyzes into volatile constituents, one of which is vanillin or ethylvanillin which enhances the flavor and aroma of low delivery cigarette smoke:

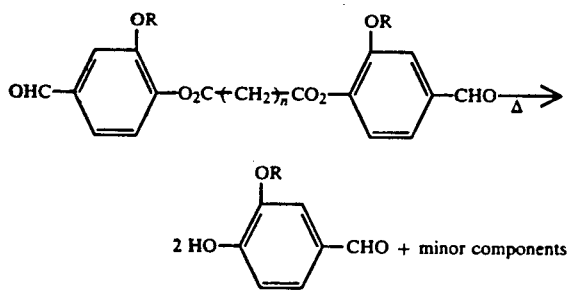

PREPARATION OF FLAVORANT-RELEASE COMPOUNDS

One method of preparing the invention di-vanillyl ester flavorant-release compounds is by the reaction of vanillin or ethylvanillin with an appropriate dicarboxyl halide.

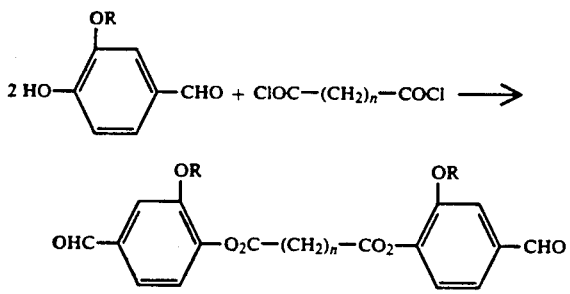

The reaction is conducted in an organic solvent medium in the presence of a mild base such as pyridine. In a typical procedure the acid halide is added to the vanillin in an inert solvent medium such as tetrahydrofuran or dimethylformamide, maintained at a temperature between about 0° C.-60° C. under an inert atmosphere.

PREPARATION OF TOBACCO COMPOSITIONS

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant-release additive corresponding to the formula:

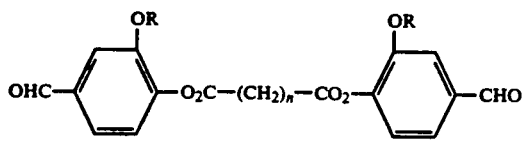

where n is an integer in the range of 0-4, and R is methyl or ethyl.

The invention di-vanillyl ester flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5-5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references Cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150° C.-750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously described hereinabove, an invention flavorant-release additive also can be incorporated in the paper wrapper of cigarette products, for the purpose of enhancing the aroma of cigarette sidestream smoke under smoking conditions. The additive can be applied to the paper wrapper in the form of a additive can be included as an ingredient during the cigarette paper making process.

A further method of incorporating a flavorant-release additive in a cigarette smoking composition is by including the additive as an ingredient in the paper wrapper sideseam adhesive formulation which is employed in cigarette fabrication.

The following Examples are further illustrative of the present invention. The specific ingredients and processing parameters are presented as being typical, and various modifications can be derived in view of the foregoing disclosure within the scope of the invention.

EXAMPLE I

This Example illustrates the synthesis of di-vanillyl oxalate.

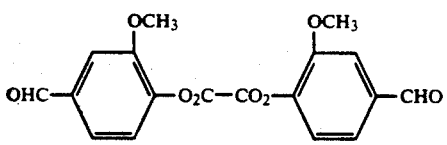

A 2-liter 3-neck flask fitted with a mechanical stirrer was charged with 76 g of vanillin, 1200 ml of methylene chloride and 40 g of pyridine. The reaction medium was cooled in an ice bath, and 100 ml of 2.0 M oxaloyl dichloride in methylene chloride was added dropwise. The reaction mixture was stirred for 30 minutes at 0° C. and then 1 hour at room temperature after the addition was complete. The resulting precipitate was filtered and the recovered solid was washed successively with 500 ml of 50% aqueous ethanol, 500 ml of 95% ethanol, and 250 ml of acetone. After air-drying, the white solid was dried at 50 mTorr, mp 207°-207.5° C. (decomposition with gas evolution), yield (96.7%). NMR Spectra confirmed the compound structure.

Anal. Calc. for $C_{18}H_{14}O_8$: C, 60.34; H, 3.94.
Found: C, 60.46; H, 3.90.

The corresponding di-ethylvanillyl oxalate compound is prepared by using ethylvanillin in place of vanillin in the synthesis procedure.

The corresponding di-vanillyl malonate is prepared by using malonoyl dichloride in place of oxaloyl dichloride in the synthesis procedure.

Pyrolysis GC/MS at 300° C. of di-vanillyl oxalate produced an essentially quantitative yield of vanillin as the only detectable product.

EXAMPLE II

This Example illustrates the synthesis of di-vanillyl succinate.

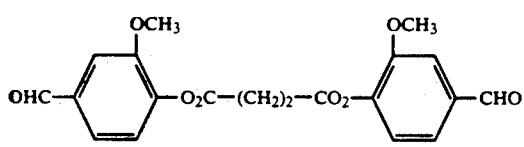

A solution of 3.1 g of succinoyl dichloride in 10 ml of ethyl acetate is added dropwise at room temperature to a stirred solution of 6.08 g of vanillin and 3.6 g of pyridine in 50 ml of ethyl acetate. The reaction mixture which contained a solid suspension was stirred for 18 hours, and then diluted with 150 ml of ethyl acetate and 100 ml of water.

The organic layer was washed successively with 150 ml of dilute hydrochloric acid, 150 ml of water, 150 ml of saturated sodium bicarbonate, and 150 ml of saturated sodium chloride. The organic extract was dried over anhydrous sodium sulfate, filtered, and concentrated on a rotary evaporator to provide 6.0 g of pale green solid. An analytically pure sample was obtained by recrystallization from hot acetone/hexane, mp, 138.5°-139° C. NMR Spectra confirmed the compound structure.

Anal. Calc. for $C_{20}H_{18}O_8$: C, 62.17; H, 4.70.
Found: C, 62.25; H, 4.70.

The corresponding di-ethylvanillyl succinate compound is prepared by using ethylvanillin in place of vanillin in the synthesis procedure.

Pyrolysis GC/MS at 300° C. of di-vanillyl succinate produced an essentially quantitative yield of vanillin, and a minor amount of other organic material. When di-vanillyl diethylmalonate was heated at 300° C. under similar conditions, the compound distilled and only a minor quantity of vanillin was detected.

EXAMPLE III

This Example illustrates the preparation of di-vanillyl glutarate.

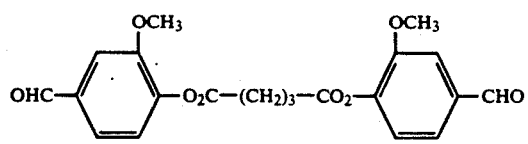

Following the synthesis procedure of Example II, 30.4 g of vanillin in ethyl acetate was reacted with 16.9 g of glutaroyl dichloride in hexane. After the reaction medium was diluted with ethyl acetate and water, the organic layer was washed in the manner previously described, and diluted with hexane. The resulting precipitate was recovered and air-dried. Recrystallization from hot acetone/hexane provided an analytically pure sample, mp, 95° C. -96° C. NMR Spectra confirmed the compound structure.

Anal. Calc. for $C_{21}H_{20}O_8$: C, 62.99; H, 5.03.
Found: C, 63.37; H, 5.09.

The corresponding di-ethylvanillyl glutarate is prepared by using ethylvanillin in place of vanillin in the synthesis procedure.

The corresponding the di-vanillyl adipate is prepared by using adipoly dichloride in place of glutaroyl dichloride in the synthesis procedure.

Pyrolysis GC/MS at 200° C. and 300° C. of di-vanillyl glutarate produced an essentially quantitative yield of vanillin, and a minor amount of other organic material. When vanillyl 2,2-dimethylhexanoate was heated at 300° C. under similar conditions, the compound distilled and only a minor quantity of vanillin was detected. A similar compound distillation was observed when vanillyl p-toluate was heated at 300° C.

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

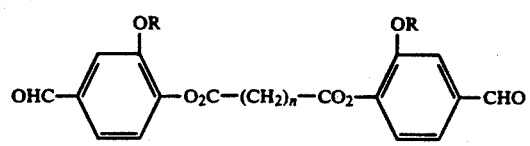

where n is an integer in the range of 0-4, and R is methyl or ethyl.

2. A smoking composition in accordance with claim 1 wherein the flavorant-release additive is di-vanillyl oxalate.

3. A smoking composition in accordance with claim 1 wherein the flavorant-release additive is di-vanillyl malonate.

4. A smoking composition in accordance with claim 1 wherein the flavorant-release additive is di-vanillyl succinate.

5. A smoking composition in accordance with claim 1 wherein the flavorant release additive is di-vanillyl glutarate.

6. A smoking composition in accordance with claim 1 wherein the flavorant release additive is di-vanillyl adipate.

7. A cigarette smoking product comprising (1) a combustible filler selected from natural tobacco, reconstituted tobacco and tobacco substitutes, and (2) a paper wrapper which has incorporated therein a flavorant-release additive corresponding to the formula:

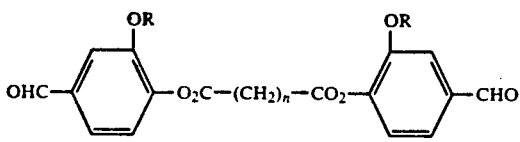

where n is an integer in the range of 0–4, and R is methyl or ethyl.

8. A cigarette smoking product in accordance with claim 7 wherein the paper wrapper contains between about 0.01–5 weight percent of flavorant-release additive.

9. A cigarette smoking product in accordance with claim 7 wherein the flavorant-release additive in the paper wrapper is di-vanillyl oxalate.

10. A cigarette smoking product in accordance with claim 7 wherein the flavorant-release additive in the paper wrapper is di-vanillyl malonate.

11. A cigarette smoking product in accordance with claim 7 wherein the flavorant-release additive in the paper wrapper is di-vanillyl succinate.

12. A cigarette smoking product in accordance with claim 7 wherein the flavorant-release additive in the paper wrapper is di-vanillyl glutarate.

13. A cigarette smoking product in accordance with claim 7 wherein the flavorant-release additive in the paper wrapper is di-vanillyl adipate.

14. A cigarette smoking product in accordance with claim 7 wherein the flavorant-release additive is a component of the sideseam adhesive of the paper wrapper.

15. A cigarette smoking product in accordance with claim 7 wherein the combustible filler contains between about 0.0001–5 weight percent, based on the weight of filler, of a flavorant-release additive corresponding to the formula:

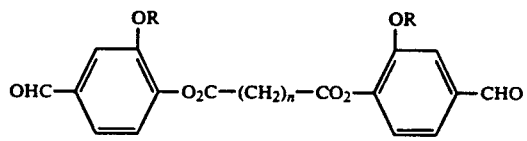

where n is an integer in the range of 0–4, and R is methyl or ethyl.

16. A cigarette smoking product in accordance with claim 15 wherein the flavorant-release additive in the combustible filler is di-vanillyl oxalate.

17. A cigarette smoking product in accordance with claim 15 wherein the flavorant-release additive in the combustible filler is di-vanillyl malonate.

18. A cigarette smoking product in accordance with claim 15 wherein the flavorant-release additive in the combustible filler is di-vanillyl succinate.

19. A cigarette smoking product in accordance with claim 15 wherein the flavorant-release additive in the combustible filler is di-vanillyl glutarate.

20. A cigarette smoking product in accordance with claim 15 wherein the flavorant-release additive in the combustible filler is di-vanillyl adipate.

21. An ester compound corresponding to the formula:

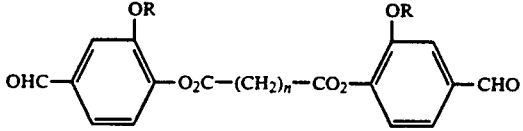

where n is an integer in the range of 0–4, and R is methyl or ethyl.

22. Di-vanillyl oxalate.
23. Di-vanillyl malonate.
24. Di-vanillyl succinate.
25. Di-vanillyl glutarate.
26. Di-vanillyl adipate.

UNITED STATES PATENT AND TRADEMARK OFFICE
CERTIFICATE OF CORRECTION

PATENT NO. : 5,137,036
DATED : Aug. 11, 1992
INVENTOR(S) : Everett W. Southwick

It is certified that error appears in the above-indentified patent and that said Letters Patent is hereby corrected as shown below:

Column 4, lines 54 (after "conditions.") - 57, should read:

--The additive can be applied to the paper wrapper in the form of a solution, or a suspension of fine particles. Alternatively, the additive can be included as an ingredient during the cigarette paper making process--.

Signed and Sealed this

Second Day of November, 1993

Attest:

BRUCE LEHMAN

*Attesting Officer*   *Commissioner of Patents and Trademarks*